(12) United States Patent
Suwito et al.

(10) Patent No.: US 8,353,876 B2
(45) Date of Patent: Jan. 15, 2013

(54) OCCLUSION RESISTANT CATHETERS

(75) Inventors: Wan Suwito, Sandy, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 584 days.

(21) Appl. No.: 12/022,923

(22) Filed: Jan. 30, 2008

(65) Prior Publication Data

US 2009/0192496 A1   Jul. 30, 2009

(51) Int. Cl.
*A61M 5/32* (2006.01)
(52) U.S. Cl. ........ 604/174; 604/177; 604/178; 604/179; 604/523; 604/524; 604/525; 604/526; 604/527; 604/533; 604/534; 604/535
(58) Field of Classification Search .......... 604/523–527, 604/174, 177, 178, 179, 264, 268, 533–535; 285/114
See application file for complete search history.

(56) References Cited

U.S. PATENT DOCUMENTS

| | | | |
|---|---|---|---|
| 3,867,937 A | 2/1975 | Schwartz | |
| 4,068,660 A | 1/1978 | Beck | |
| 4,280,500 A | 7/1981 | Ono | |
| 4,610,674 A | 9/1986 | Suzuki et al. | |
| 4,838,873 A | 6/1989 | Landskron et al. | |
| 4,846,812 A | 7/1989 | Walker et al. | |
| 5,405,338 A | 4/1995 | Kranys | |
| 5,658,253 A * | 8/1997 | Piontek et al. | 604/170.02 |
| 5,827,239 A * | 10/1998 | Dillon et al. | 604/263 |
| 6,074,379 A * | 6/2000 | Prichard | 604/524 |
| 6,102,890 A | 8/2000 | Stivland et al. | |
| 6,156,054 A | 12/2000 | Zadno-Azizi et al. | |
| 6,217,566 B1 | 4/2001 | Ju et al. | |
| 6,245,098 B1 | 6/2001 | Feeser et al. | |
| 6,273,404 B1 | 8/2001 | Holman et al. | |
| 6,387,075 B1 | 5/2002 | Stivland et al. | |
| 6,503,353 B1 | 1/2003 | Peterson et al. | |
| 6,511,462 B1 | 1/2003 | Itou et al. | |
| 6,575,958 B1 | 6/2003 | Happ et al. | |
| 6,579,221 B1 | 6/2003 | Peterson | |
| 6,663,614 B1 | 12/2003 | Carter | |
| 6,824,553 B1 | 11/2004 | Samson et al. | |
| 6,893,456 B2 | 5/2005 | Lumauig | |
| 7,115,183 B2 | 10/2006 | Larson et al. | |
| 2005/0209581 A1 | 9/2005 | Butts et al. | |
| 2006/0064159 A1 * | 3/2006 | Porter et al. | 623/1.24 |
| 2006/0259012 A1 | 11/2006 | Propp et al. | |

FOREIGN PATENT DOCUMENTS

| | | |
|---|---|---|
| EP | 0 227 230 A1 | 7/1987 |
| EP | 1 466 645 A2 | 10/2004 |
| WO | WO9616690 | 6/1996 |
| WO | WO9916498 | 4/1999 |
| WO | WO2004071568 A1 | 8/2004 |
| WO | WO2006012446 A2 | 2/2006 |
| WO | WO2006100442 A1 | 9/2006 |

* cited by examiner

*Primary Examiner* — Bhisma Mehta
*Assistant Examiner* — Larry R Wilson
(74) *Attorney, Agent, or Firm* — Jeanne Lukasavage; Craig Metcalf; Kirton McConkie

(57) ABSTRACT

A device and method for preventing an occlusion of a catheter including a catheter adapter and a catheter where a flexured portion of the catheter is supported by a bending surface of the catheter adapter. The flexured portion of the catheter may also include a maximum insertion length mark and/or a flexible support member to support and strengthen the flexured portion of the catheter against occlusions. A bending surface is provided over which a flexured portion of the catheter may gently bend to accommodate the transition of the catheter from the catheter adapter to the insertion site without occluding the catheter.

13 Claims, 10 Drawing Sheets

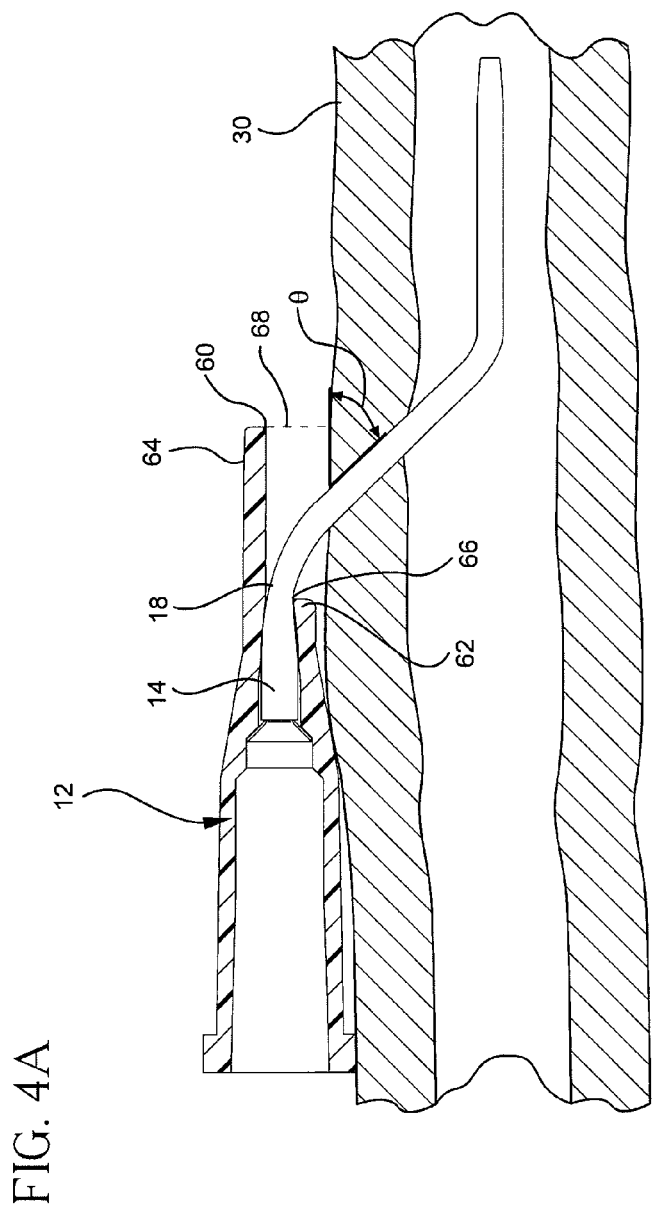

OCCLUSION RESISTANT CATHETERS

BACKGROUND OF THE INVENTION

The present disclosure relates generally to infusion therapy with vascular access devices, and relates specifically to infusion therapy with intravenous catheters. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Intravenous therapy is facilitated by vascular access devices located outside the vascular system of a patient (extravascular devices). Extravascular devices that may access a patient's peripheral or central vasculature, either directly or indirectly include closed access devices, such as the BD Q-SYTE closed Luer access device of Becton, Dickinson and Company; syringes; split access devices; catheters; and intravenous (IV) fluid chambers. A vascular device may be indwelling for short term (days), moderate term (weeks), or long term (months to years). A vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter is commonly incorporated into a catheter adapter to aid in the ease of use, accessibility and utility of the catheter. A catheter adapter is generally a rigid, plastic, tubular member adapted to house one end of the catheter such that one end of the catheter is supported by the catheter adapter; the body and tip of the catheter extending beyond a first end of the catheter adapter. The catheter adapter generally further comprises a second end adapted to receive additional infusion components for use with the catheter. For example, the second end of a catheter adapter may include a set of threads for attaching an intravenous line or for coupling a syringe to the catheter adapter thereby providing access to the patient via the attached catheter.

The catheter may be inserted transcutaneously or may be surgically implanted beneath the patient's skin. When inserted transcutaneously, the insertion of the catheter is commonly aided by a hypodermic needle. The hypodermic needle is commonly housed inside the lumen of the catheter such that the gauge of the needle approximates the inner diameter of the catheter. The needle is positioned within the catheter such that the needle tip extends beyond the tip of the catheter whereby the needle is used to penetrate the patient's vein and provide an opening for insertion of the catheter.

The needle and catheter generally approach the patient's vein at an angle of about 30° wherein the needle initially punctures the patient's epidermis and then continues into the vein. Once the needle and catheter tip enter the patient's vein, the needle and catheter are then repositioned so that the needle and catheter are brought into a position generally parallel with the patient's vein so that the needle and catheter may be inserted into the lumen of the patient's vein. When the catheter has been properly positioned within the patient's vein, the needle is removed from the lumen of the catheter and the catheter adapter is secured to the patient to prevent premature removal of the catheter.

Typically the catheter adapter is secured to the patient by fastening the catheter adapter to the patient's skin via tape and/or steri-strips. In securing the catheter adapter to the patient's skin, the root region of the catheter must arch to accommodate the catheter's transition from the generally parallel, secured orientation of the catheter adapter, to the insertion angle of the catheter; an angle of approximately 30°. General practice requires that the catheter be inserted into a patient such that an extended section of catheter is left between the patient and the catheter adapter to allow for transitional arching of the catheter. Several issues exist regarding the need for this exposed, archable length of catheter.

First, in making this arch, the catheter is biased towards the patient's skin and thus the root region of the catheter experiences leverage forces wherein the catheter acts as a lever and the first end of the catheter adapter acts as a fulcrum exerting an upward force on the root region of the catheter. This upward force of the first end of the catheter adapter is undesirable due to the likelihood of occlusion of the root region of the catheter against the more rigid catheter adapter. Occlusion typically occurs as the patient and or the catheter is moved thereby increasing the angle of insertion in relation to the fixed position of the catheter adapter. For example, if the repositioning of the catheter and/or patient inserts the catheter further into the patient, the archable length of catheter between the patient and the catheter adapter is decreased thereby increasing the angle of insertion and the upward force of the immobilized catheter adapter on the root region of the catheter. As the angle of insertion increases the upward force of the catheter adapter also increases until such point that the structural rigidity of the catheter wall is overcome and the catheter kinks in order to continue accommodating the catheter's transition from the catheter adapter into the patient.

Occlusion of the catheter is undesirable as occlusions serve to slow or stop the flow through the catheter thereby creating undesirable backpressures that may cause the infusion system to malfunction and/or be damaged. Additionally, occlusions reduce the efficiency of the infusion system which could effect the treatment and/or diagnosis of the patient.

Second, due to the exposed nature of the arched catheter section, the exposed catheter section may become contaminated and pose a health risk to the patient. For example, an exposed section of catheter may become contaminated and then be inserted into the patient as the patient and/or catheter is readjusted due to normal use by the patient and/or technician. To reduce the likelihood of contamination and subsequent exposure to the patient, technicians seek to minimize the length of exposed catheter by initially over-inserting the catheter into the patient. In reducing the length of exposed catheter, the upward force of the first end of the catheter adapter is increased thereby increasing the likelihood of occlusion within the root region of the catheter.

Contamination of the catheter and/or patient is undesirable for obvious reasons, the most obvious being that contamination may lead to secondary infection and/or complications unanticipated by the treating physician. Furthermore, a contaminated catheter may introduce a virus and/or bacteria to the patient that may conflict with the patient's primary therapy such that the patient is unable to receive further needed treatment.

Therefore, a need exists for systems and methods that prevent occlusions at the root region of the catheter, prevent over-insertion of the catheter and prevent contamination of the same.

BRIEF SUMMARY OF THE INVENTION

The occlusion resistance catheters according to the invention overcome the problems of the prior art by providing additional support to the root region of the catheter and/or marks indicating a maximum point of insertion. Problems in the art may also be addressed by modifying the tip of the catheter adapter to prevent catheter occlusion due to over-insertion of the catheter.

The occlusion resistance catheters of the present invention generally include a catheter tube. The catheter tube is attached to a catheter adapter to aid in the placement and support of the catheter in a patient's vascular system. In one embodiment, the catheter tube may include a variety of materials including silicone, IntiSilf silicone, polyurethane, and polyethylene. In another embodiment, the catheter tube may also include a rounded tip or a tip with square corners. In a specific embodiment, the catheter tube is silicone and includes a rounded tip. The catheter tube has an inner diameter and an outer diameter, each of which may be selected based on the needs of the user. For example, in one embodiment the inner diameter is selected to accommodate a specific gauge of needle such that the needle may be slidably housed within the catheter.

The catheter tube material may also be impregnated or striated with an additional material for added resistance of occlusions and/or to provide a function. One such function is to add radiological detection via a radiopaque material. In one specific embodiment, the catheter tube is striated with barium sulfate thereby providing radiological detection of the catheter tube within the patient. In another specific embodiment, the material of the catheter tube is impregnated with barium sulfate in a spiral formation. In this manner, the impregnated material provides additional strength the to catheter tube to prevent occlusion of the catheter. The barium also provides for radiological detection of the catheter tube within the patient. In this embodiment, the spiral formation comprises only the root region of the catheter such that the spiral formation lends additional strength to this occlusion-prone region. Additionally, the spiral formation serves as an insertion marker where the distal end of the spiral serves as an insertion stop-mark. This aids the technician in preventing over-insertion of the catheter and insuring that the root region remains free of occlusions.

The catheter tube was attached to a first end of a catheter adapter such that the catheter tube in the catheter adapter comprise a single unit. The catheter tube may be attached to the catheter adapter using a variety of methods including heated tool, hot gas, vibration, spend, ultrasonic, induction, radio frequency, microwave, resistance, extrusion, electrocution, infrared, laser welding, mechanical fastening, and/or chemical bonding. In one embodiment, the catheter tube is fixedly attached to the catheter adapter using one or more of a variety of methods including heated tool, hot gas, ultrasonic, induction, radio frequency, microwave, resistance, extrusion, electro fusion, infrared, laser welding, and/or chemical bonding. In one embodiment, the catheter tube is attached to the catheter adapter via a mechanical fastener. The catheter tube is inserted into the catheter adapter and a tubing insert is inserted into the end of the catheter tube such that a fluid tight attachment is formed. The catheter adapter may include a variety of materials including polypropylene, polyvinyl chloride, and/or polyethylene. In one specific embodiment, the catheter adapter is polypropylene.

The catheter adapter is generally cylindrical with an opening at a first and a second end, the second end being opposite to the first end of the catheter adapter. The first end comprises an opening through which the catheter tube extends. The first end of the catheter adapter may be modified to accommodate the catheter in bending without resulting in an occlusion and/or a restriction of the flow through the catheter. Typical positioning of a transcutaneous catheter requires that the catheter bend to accommodate a transition from the catheter adapter to the insertion site. For example, general practice requires that a catheter is inserted into a patient's vein at an insertion angle of about 30°. Once the catheter reaches the lumen of the vein, the catheter is brought parallel to the patient's vein and the catheter is further inserted into the patient's vein until the desired position is reached. To prevent premature removal of the catheter, the catheter adapter is secured to the patient via adhesive tape or steri-strips. This assures that the body of the catheter adapter is generally parallel with the patient's skin thereby creating an insertion angle between the transdermal portion of the catheter and the body of the catheter adapter.

To accommodate this insertion angle, the catheter must bend from the first end of the catheter adapter to the insertion site on the patient. To prevent occlusion of and/or a restriction of the flow though the catheter, the bend must be gentle and in an arch-like fashion. Prevention of an occlusion is typically accomplished by preventing over-insertion of the catheter thereby ensuring that a sufficient, flexured length of catheter is uninserted so that a gentle arch may be formed. Over-insertion of the catheter is commonly due to either an attempt to minimize contamination of exposed catheter, or due to subsequent movement of the patient. However, the present invention provides for modifications to the tip of the catheter adapter and catheter that further decrease the likelihood of occlusion at the flexured portion of the catheter and general unnecessary over-insertion.

For example, in one embodiment the tip of the catheter adapter is modified to include a chamfered and/or rounded opening such that the catheter adapter tip opening is less than 90°. As such, the distance between the root region of the catheter and the catheter adapter tip opening is increased thereby allowing the catheter to bend more sharply before contacting the catheter adapter tip and causing an occlusion. This allows the catheter to be inserted further into the patient thereby reducing the area of exposed catheter subject to contamination. The chamfered and/or rounded opening may also provide a bending surface to support the flexured portion of the catheter such that the flexured portion of the catheter may bend along the contour of the bending surface. This provides additional support to the flexured portion and prevents occlusion.

In another embodiment, the tip of the catheter adapter is modified such that a lower half of the tip is removed, thereby allowing the catheter to bend more sharply before contacting the catheter adapter tip and causing an occlusion. Additionally, the overhanging upper half of the tip provides a shielding function. Thus, the catheter may be inserted into a patient such that the upper half of the tip overhangs the uninserted, flexured portion of the catheter, reducing contamination of the exposed catheter. Additionally, the opening of the remaining lower half may be chamfered and/or rounded to provide a contoured, bending surface to aid in supporting the catheter's flexured portion in making a curved transition from the catheter adapter to the insertion site so as to further prevent an occlusion.

In addition to modifying the tip of the catheter adapter, the catheter may be modified to prevent over-insertion during catheterization. For example, in one embodiment the flexured portion of the catheter is marked for a maximum insertion length wherein upon insertion of the catheter up to the mark, a sufficient length of catheter remains uninserted so as to prevent an occlusion. This mark may include an internal and/or an external mark comprising a contrasting color. Additionally and/or alternatively the mark may comprise a physical feature such as a notch, a ferrule, a crimp, and/or a texture. In one embodiment, the mark is printed on the catheter such that a contrasting colored ink is applied to the outer and/or inner surface of the catheter. In another embodiment, the outer surface and/or inner surface of the catheter is marked via laser etching. In one specific embodiment, the mark is an external, contrasting color comprising at least one band printed on the outer surface of the catheter. In each embodiment, the mark comprises a material and/or a physical feature that is compatible with an infusion system and materials used therein.

One final modification may include modifying the catheter to include a physical feature that strengthens the occlusion-prone root region of the catheter. For example, in one embodiment an exterior sleeve of shrink tubing is included over the flexured portion of the catheter such that the flexured portion is strengthened against over-bending and resultant occlusion. The properties of the shrink tubing may vary such that the tubing may be flexible or semi-flexible so as to allow the covered catheter to flex in a controlled manner, as necessary.

Additionally or alternatively, the shrink tubing may vary in thickness. For example, the shrink tubing may be relatively thin or relatively thick such that the degree of flexibility is greater with a thinner shrink tubing. The shrink tubing may also include varying thicknesses, for example the shrink tubing may be tapered wherein the flexibility of the shrink tubing varies throughout the taper such that the thicker portions of the taper are less flexible than the thinner portions of the taper. The shrink tubing may be comprised of any thermoplastic material such as polyolefin, fluoropolymer (such as FEP, PTFE or Kynar), PVC, neoprene, silicone elastomer or Viton.

The shrink tubing may be positioned on the catheter such that the terminal end of the shrink tubing serves a marking function for maximum insertion length of the catheter. For example, the shrink tubing may be positioned over the flexured portion of the catheter to mark a maximum insertion point such that upon insertion of the catheter up to the mark, a sufficient length of catheter remains uninserted so as to prevent an occlusion. The shrink tubing may be of a contrasting color so as to serve as a visual marker. The shrink tubing may be physically larger than the catheter such that the shrink tubing is too large to be inserted into the catheter insertion site.

In another embodiment, the catheter is modified to include an embedded coil of supportive material throughout the flexured portion of the catheter. For example, in one embodiment the flexured portion of the catheter is designed and manufactured to include a coil of supportive material embedded within the walls of catheter. As such, the coiled material forms multiple loops around the circumference of the catheter lumen in a continuous and supportive manner. In this embodiment, the supportive material may include a rigid, semi-rigid, semi-flexible and/or flexible radiopaque material such as wire. The wire may comprise stainless steel, copper, aluminum, lead, tungsten, platinum, gold, silver, and/or tantalum. Additionally, the coil may be formed within the wall of the catheter by injection during the manufacturing process. The injected material may include a radiopaque material such as bismuth oxychloride, bismuth subcarbonate, bismuth trioxide, and/or barium sulfate.

The number and density of coils may vary depending upon the physical properties of the chosen coil material as well as the desired flexibility of the coil and the desired length of the coil. Density of coils is defined as coils per centimeter, where the greater the number of coils per centimeter, the greater the supportive effect of the coil to the root region of the catheter. In one embodiment the number and density of coils is selected so as to provide a semi-flexible coil that is supportive to the root region of the catheter. This provides flexibility to the flexured portion of the catheter such that the flexured portion may bend to accommodate insertion of the catheter without occlusion. In another embodiment, the number and density of coils is selected so as to flexibly support the root region of the catheter against occlusions and provide a maximum insertion length mark. Thus, the catheter may be inserted up to the mark thereafter leaving a sufficient length of catheter uninserted to prevent an occlusion.

Further embodiments include combinations of the aforementioned embodiments to achieve a desired effect. For example, in one embodiment a catheter adapter tip with a chamfered bending surface is combined with a catheter comprising a maximum insertion length mark. In another embodiment, a catheter adapter tip, with a removed lower half, is combined with a catheter comprising an embedded coil of supportive material throughout the flexured portion of the catheter. In another embodiment, a catheter comprising an embedded coil of supportive material throughout the flexured portion of the catheter is combined with an external marking indicating a maximum insertion length.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 4a is a cross-section view of an embodiment of a catheter adapter tip wherein the tip is stepped.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
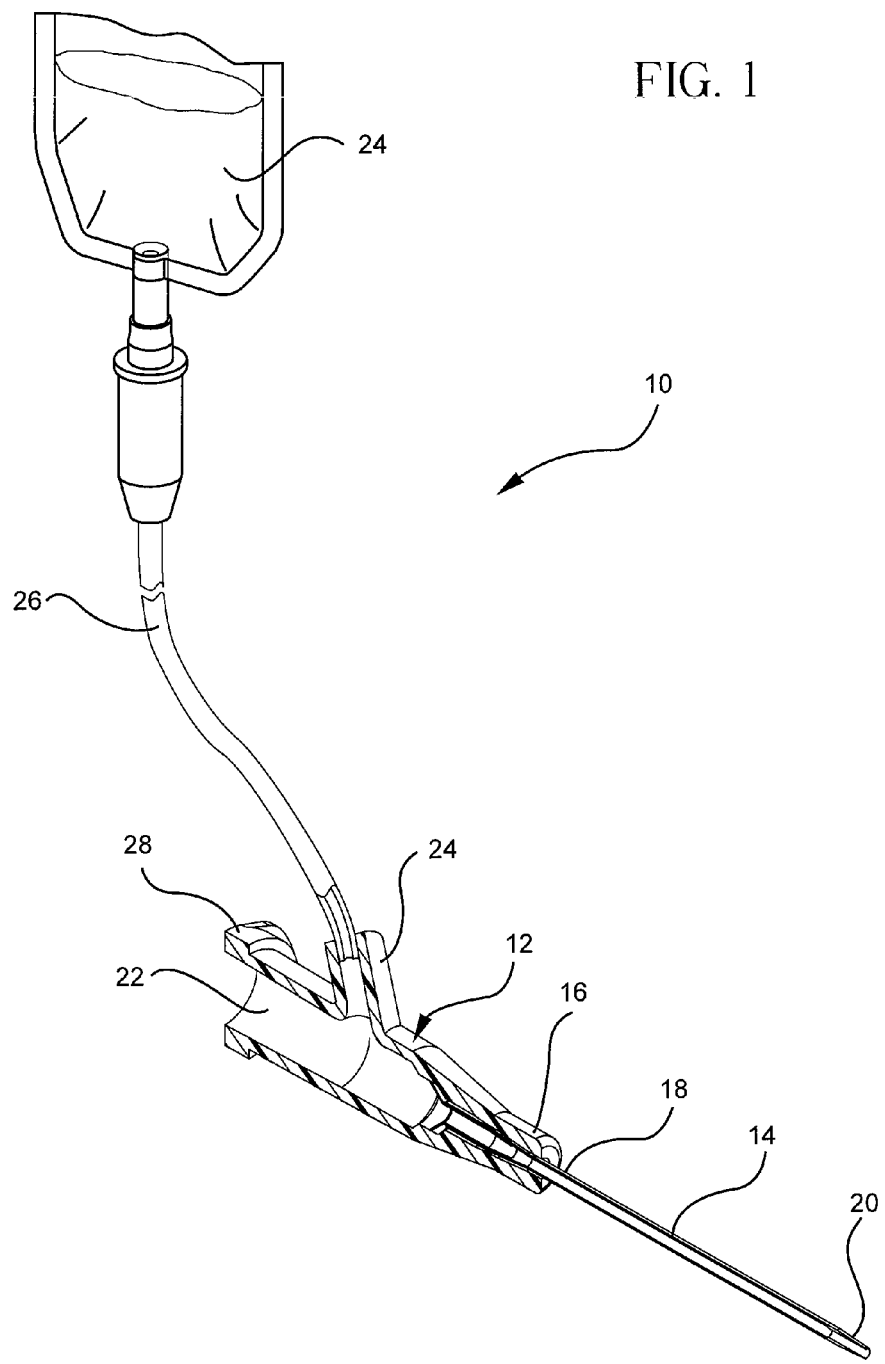
FIG. 1 is a perspective view of a catheter and a catheter adapter as incorporated into an infusion system.

Referring now to FIG. 1, an infusion system 10 is illustrated wherein the infusion system 10 comprises a catheter adapter 12, a section of intravenous tubing 26 and an intravenous (IV) fluid source 24. The catheter adapter 12 is connected to the IV fluid source 24 via the section of IV tubing 26, as illustrated. The infusion system 10 may also include additional components and/or subcomponents as necessary for various application and/or procedures. For example, a peristaltic pump may be incorporated into the infusion system 10 for high pressure/high volume infusion procedures.

The catheter adapter 12 is generally tubular and comprises a rigid material. The catheter further comprises a body 22 having a first end 16 and a second end 28. The first end 16 is generally tapered and comprises an exposed catheter 14. The second end 28 generally comprises an access port for accessing a lumen 46 of the catheter adapter body 22. Additional features of the catheter adapter 12 may include a lateral access port 42 as illustrated. The lateral access port 42 may be connected to the section of IV tubing 26 for establishing a fluid communication between the IV fluid source 24 and the lumen 46 of the catheter adapter 12.

The lumen 46 of the catheter adapter 12 houses a portion of the catheter 14 in a fluidtight manner. As such, a fluid from the I.V. fluid source 24 may flow through the catheter adapter lumen 22 and into the catheter 14 without interruption. The catheter adapter 12 may also be configured to house an introducer needle for inserting the catheter 14 into a patient.

The catheter 14 is generally tubular and flexible comprising a shaft of uniform thickness having a length. The length is defined by the distance between the flexured portion 18 of the catheter 14 and the catheter tip 20. The catheter 14 further comprises a lumen 56. The diameter of the lumen 56 may vary and is selected to accommodate a desired flow rate and/or pressure from the I.V. fluid source 24. The catheter 14 further comprises a flexured portion 18. The flexured portion 18 is defined as the portion of the catheter 14 that abuts the first end 16 of the catheter adapter 12. As discussed above, the proximity of the flexured portion 18 to the first end 16 of the catheter adapter 12 makes the flexured portion 18 prone to occlusion. This is because the first end 16 of the catheter adapter 12 exerts an upward force on the flexured portion 18 when the catheter 14 is moved independent of and relative to the generally horizontal plane of the catheter adapter 12.

The catheter further comprises a catheter tip 20. The catheter tip 20 comprises an opening selected to provide clearance for an introducer needle. The diameter of the opening is selected to provide minimal tolerance between the outer surface of the needle and the inner surface of the catheter tip 20 opening. As such, the needle tip may provide a sufficiently sized access route into a patient's vein 32 as illustrated in FIGS. 2-5c.

Figure 2:
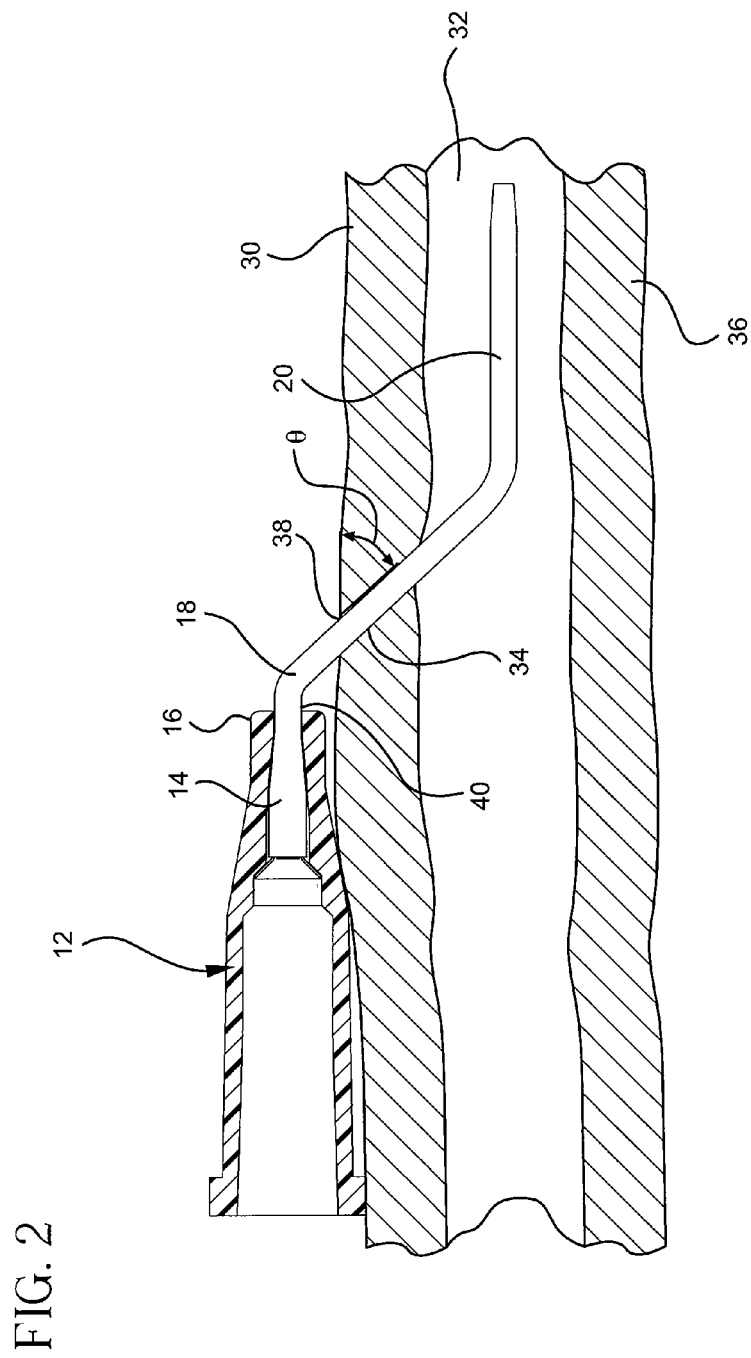
FIG. 2 is a partial perspective view of a catheter as inserted into a patient, shown in cross-section.

Referring now to FIG. 2, a catheter adapter 12 is illustrated in a generally horizontal orientation. The catheter adapter 12 is secured to a patient 30 and the catheter tip 20 is inserted into the patient's vascular system 32. The catheter 14 further comprises a transdermal section 34. The transdermal section 34 of the catheter 14 is positioned within the patient's dermal layer 36 at a determined angle of insertion θ. The angle of insertion θ may include any angle θ necessary to introduce the catheter 14 into the patient's vascular system 32. For example, an angle of insertion θ may be selected within the range of 1° to 90°, with a preferable angle of insertion θ of about 30°.

Following insertion of the catheter 14, the flexured portion 18 of the catheter 14 is bent in a general arch shape. This shape is necessary to accommodate the transition of the catheter 14 from the catheter adapter 12 first end 16 to the catheter insertion site 38. An catheter root 40 is located on the underside of the arched flexured portion 18. The arched flexured portion 18 of the catheter 14 abuts the rigid, first end 16 of the catheter adapter 12.

The catheter root 40 experiences leverage forces as the catheter 14 is inserted into the insertion site 38. Thus, the catheter 14 acts as a lever and the rigid first end 16 of the catheter adapter 12 acts as a fulcrum exerting an upward force on the catheter root 40 of the flexured portion 18. As the catheter 14 is inserted further into the insertion site 38, the upward force of the first end 16 increases until such time that the upward force is greater than outward force of the catheter 14 tube wall. At that time, a partial kink occurs at the catheter root 40 thereby causing an occlusion of the catheter 14.

An occlusion of the catheter 14 may be caused by over-insertion of the catheter 14 into a patient 30. Over-insertion of the catheter 14 results in increased upward force of the first end 16 of the catheter adapter 12. The increased upward force results in a greater likelihood of occlusion for the catheter 14 at the catheter root 40. There are several ways by which a catheter 14 may be over-inserted. For example, a catheter 14 may be over-inserted by a technician seeking to minimize the amount of exposed flexured portion 18. A technician may desire to minimize the amount of exposed flexured portion 18 for reasons of sanitation and/or for prevention of infection at the insertion site 38. Additionally, a catheter 14 may become over-inserted inadvertently due to movements of the patient 30.

Figure 3A:
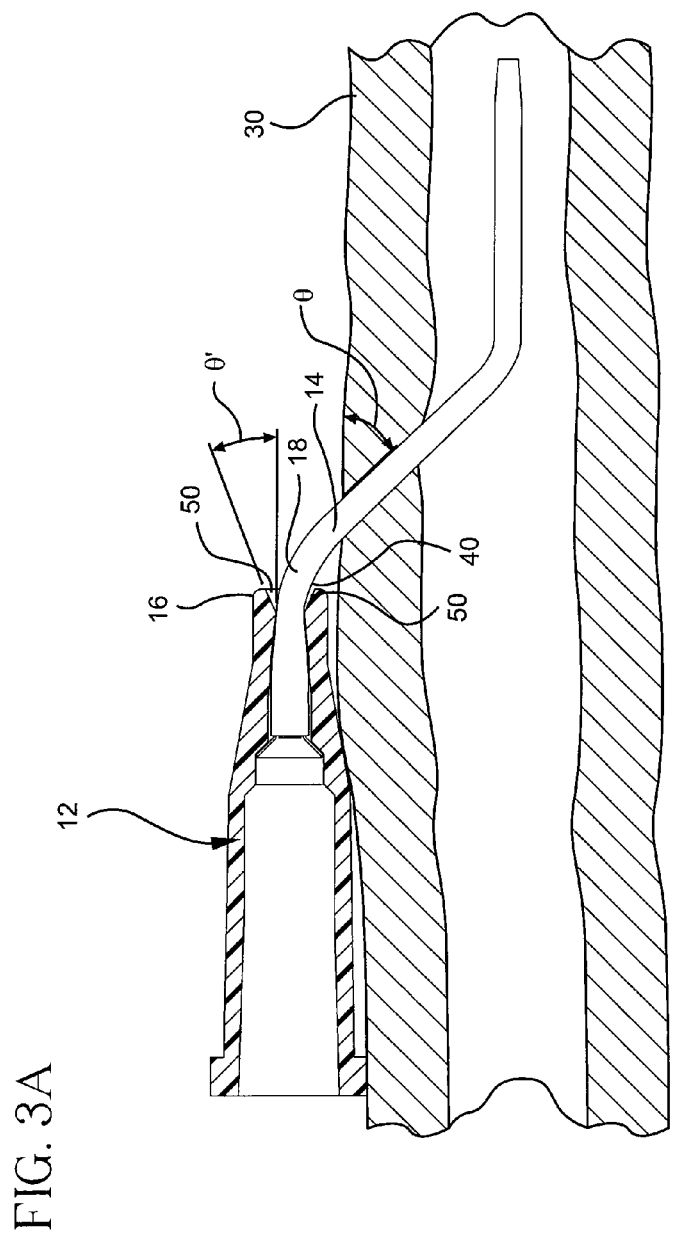
FIG. 3a is a cross-section view of an embodiment of a catheter adapter tip wherein the tip is chamfered.

Referring now to FIG. 3a, a first embodiment of an occlusion resistant catheter adapter is illustrated. In this embodiment, the catheter adapter tip opening 50 is chamfered such that the tolerance between the first end 16 of the catheter adapter 12 and the flexured portion 18 of the catheter is increased. Thus, the flexured portion 18 of the catheter 14 may bend more sharply before the catheter root 40 contacts the catheter adapter tip opening 50 resulting in an occlusion. In one embodiment, the catheter adapter tip opening 50 is chamfered at an angle θ' which is less than 90° relative to the generally horizontal plane 52. The chamfered opening 50 permits a greater length of catheter 14 to be inserted before an occlusion occurs due to the delayed contact of the tip opening 50 and the catheter root 40. Therefore, as the flexured portion 18 of the catheter 14 is further inserted into the patient 30, the flexured portion 18 is allowed to bend to a greater degree before contacting and pivoting on the tip opening 50 resulting in an occlusion of the catheter 14 at the flexured portion 18.

Figure 3B:
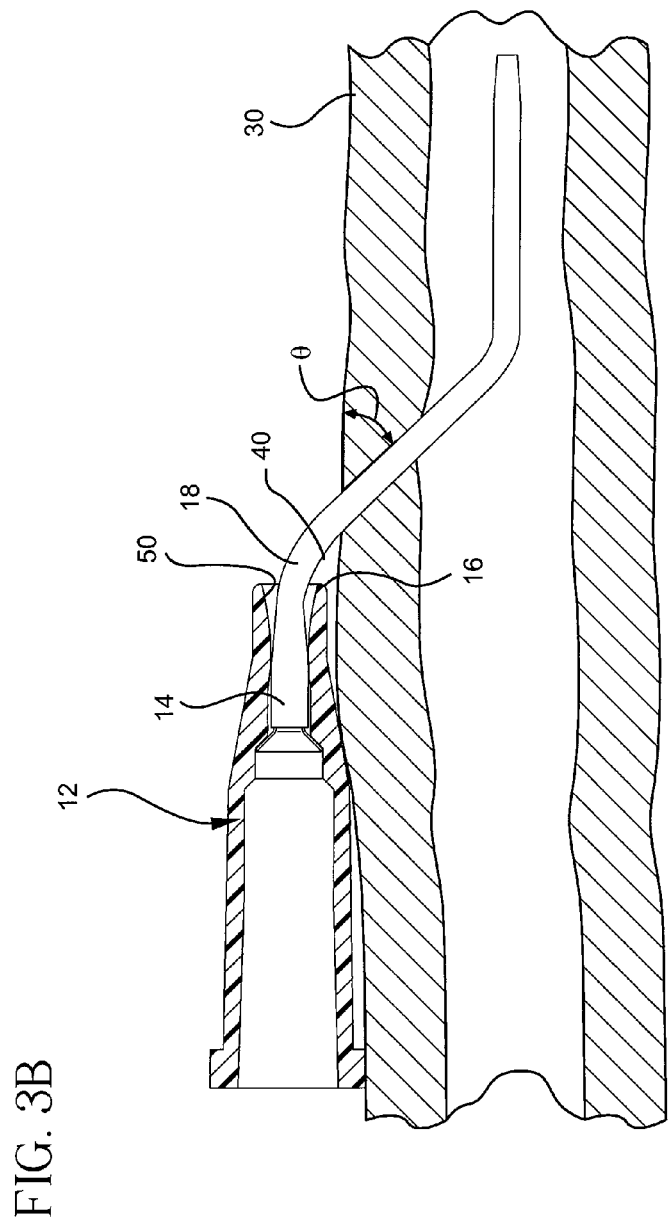
FIG. 3b is a cross-section view of an embodiment of a catheter adapter tip wherein the tip is contoured.

Referring now to FIG. 3b, a variation on the embodiment of FIG. 3a is illustrated. In this embodiment, the catheter adapter tip opening 50 is rounded such that the opening comprises an arch of no more than 90°. The degree of curvature is selected to support the flexured portion 18 of the catheter 14 in maintaining an angle of insertion θ, within the desired range. In this embodiment, the flexured portion 18 of the catheter 14 is bent over and along the contour of the rounded opening 50. The flexured portion 18 is supported by the rounded opening 50 in maintaining the necessary degree of curve for the catheter 14 so as to avoid an occlusion and maintain the optimal degree of insertion θ. The rounded opening 50 minimizes the fulcrum function of the first end 16 of the catheter adapter 12 on the flexured portion 18 of the catheter 14 such that the catheter 14 may be maximally inserted into the patient 30 with minimal upward force of the first end 16 on the catheter root 40. This minimizes the likelihood of occlusion at the catheter root 40.

Referring now to FIG. 4a, a second embodiment of an occlusion resistant catheter adapter is illustrated wherein the catheter adapter tip opening 60 is stepped such that the upper portion 64 of the opening 60 extends outwardly further than the bottom portion 62 of the opening 60. In this embodiment, the catheter 14 extends beyond the bottom portion 62 of the opening 60, the catheter 14 comprising a flexured portion 18 that is unsupported by the catheter adapter 12. Thus the flexured portion 18 may bend towards the patient 30 to maintain an optimal angle of insertion θ, within the desired range. The upper portion 64 of the opening 60 is extended such that the upper portion 64 provides a shielding function. The uninserted portion of the flexured portion 18 is shielded by the overhanging upper portion 64. The overhanging upper portion 64 is configured to extend beyond the insertion site 38 thus providing a barrier 68 for the uninserted portion of the flexured portion 18. As configured, the current embodiment eliminates the need for over-insertion of the catheter 14 for the purpose of protecting the uninserted portion of the flexured portion 18. This is accomplished by overhanging an upper portion 64 of the opening 60. In this embodiment, the catheter 14 is advanced into the patient 30 until such a position that the upper portion 64 of the opening 60 is shielding the exposed flexured portion 18 of the catheter 14. At this point, the advancement of the catheter 14 into the patient 30 ceases thereby preventing an occlusion at the catheter root 66.

Figure 4B:
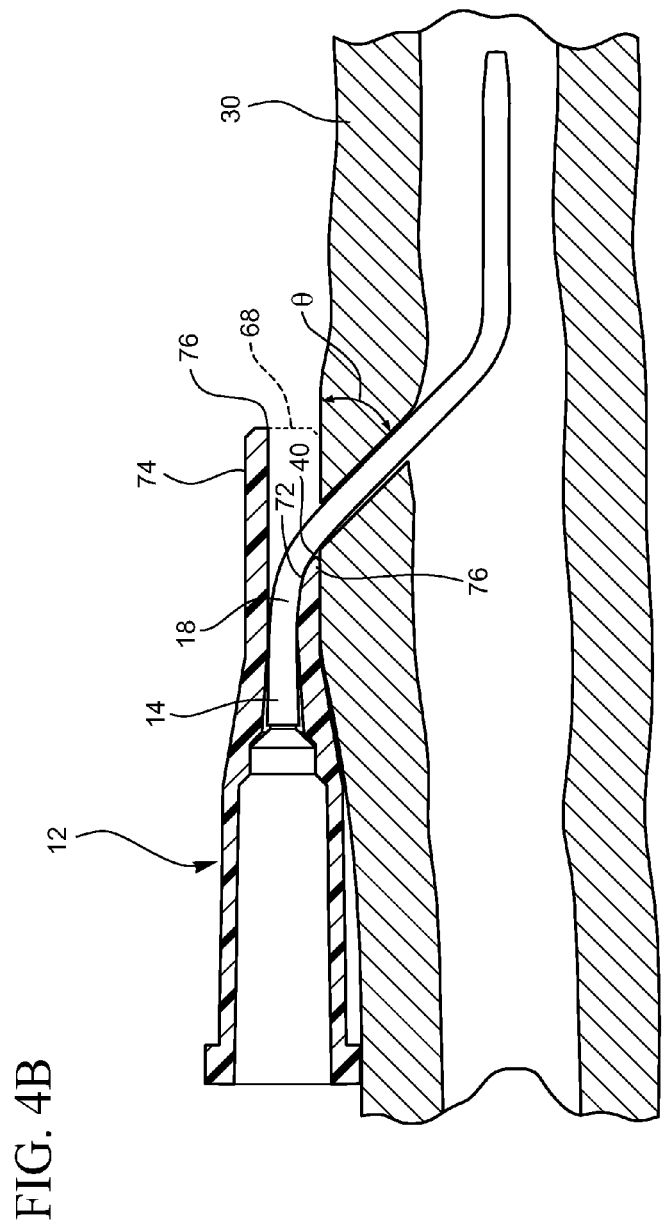
FIG. 4b is a cross-section view of an embodiment of a catheter adapter tip wherein the tip is stepped and the lower half of the tip is contoured.

Referring now to FIG. 4b, a variation on the embodiment is illustrated wherein the lower portion 72 comprises a bending surface modified to include a rounded edge or a chamfered edge. The lower portion 72 of the opening comprises an arch of no more than 90°. The degree of curvature is selected to support the flexured portion 18 of the catheter 14 in maintaining an angle of insertion θ, within the desired range. In this embodiment, the flexured portion 18 of the catheter 14 is bent over and along the contour of the rounded lower portion 72. The flexured portion 18 is supported by the rounded lower portion 72 in maintaining the necessary degree of curve for the catheter 14 so as to avoid an occlusion and maintain the optimal degree of insertion θ. The rounded lower portion 72 minimizes the fulcrum function of the inner surface of the catheter adapter 12 opening 76 on the flexured portion 18 of the catheter 14. As such, the catheter 14 may be maximally inserted into the patient 30 with minimal upward force of the inner surface of the catheter adapter 12 opening 76 on the catheter root 40. This minimizes the likelihood of occlusion at the catheter root 40.

Figure 5A:
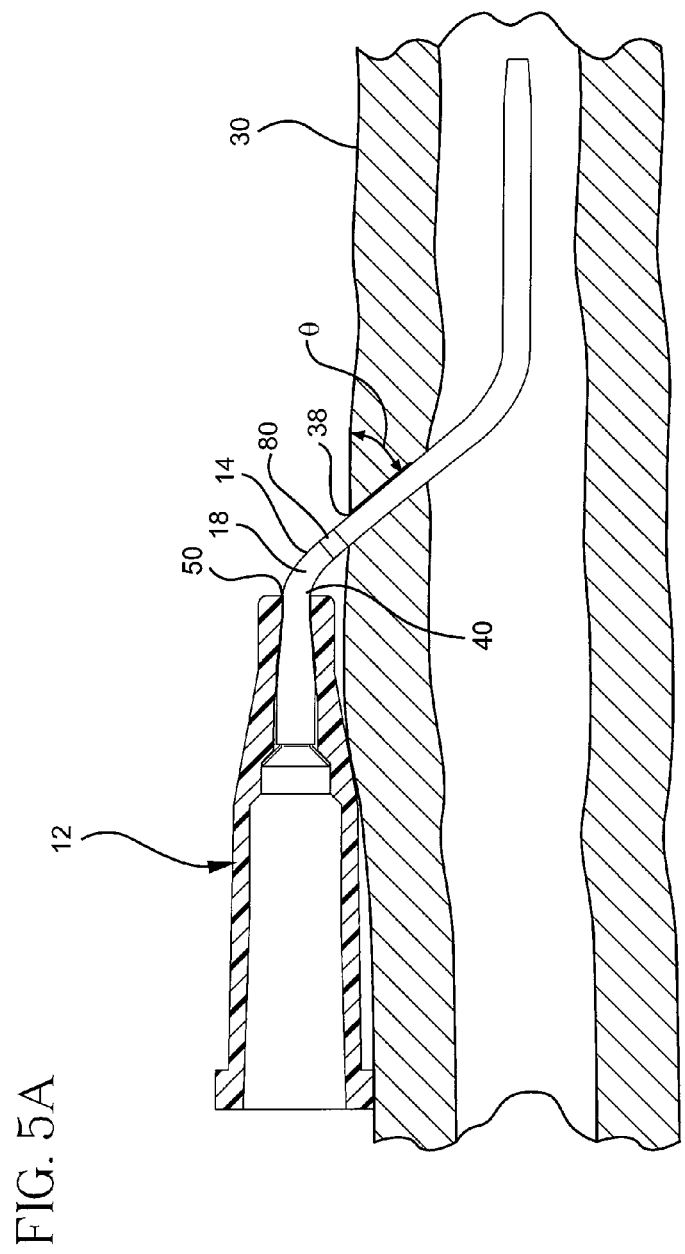
FIG. 5a is a perspective view of a catheter modified to include a maximum insertion length mark.

Referring now to FIG. 5a, a catheter 14 is illustrated as inserted into a patient 30 at an angle of insertion θ, within the desired range. The catheter 14 is incorporated into a catheter adapter 12 using a method common to one of ordinary skill in the art. The catheter 14 comprises a flexured portion 18. The flexured portion 18 is defined as the uninserted section of the catheter 14 between the first end 16 of the catheter adapter tip opening 50 and the catheter insertion site 38 of the patient 30. The catheter 14 further comprises a mark 80 to indicate a maximal insertion length for the catheter 14. When the catheter 14 is inserted up to the mark 80, a sufficient length of catheter remains uninserted. As so inserted, the flexured portion 18 may form a gentle arch thus preventing an occlusion of the catheter 14, at the catheter root 40, due to over-insertion of the catheter 14.

In one embodiment, the mark 80 comprises at least one band of a contrasting color and/or shade. The at least one band may be applied to the catheter by a plurality of techniques including ink printing, laser printing, injection molding, plastic impregnation, and laser etching. In another embodiment, the mark 80 comprises at least one physical feature such as a notch, a ferrule, a crimp and/or a texture. In this embodiment, the physical feature provides a visual and/or a tactile mark to indicate a maximum insertion length. In each embodiment, the mark 80 is positioned along the catheter 14 at a location determined to provide an optimal insertion length. This mark 80 ensures that upon insertion of the catheter 14 up to the mark 80, the flexured portion 18 of the catheter 14 forms a gentle arch to accomplish an occlusion free transition of the catheter 14 from the catheter adapter 12 to the insertion site 38.

Figure 5B:
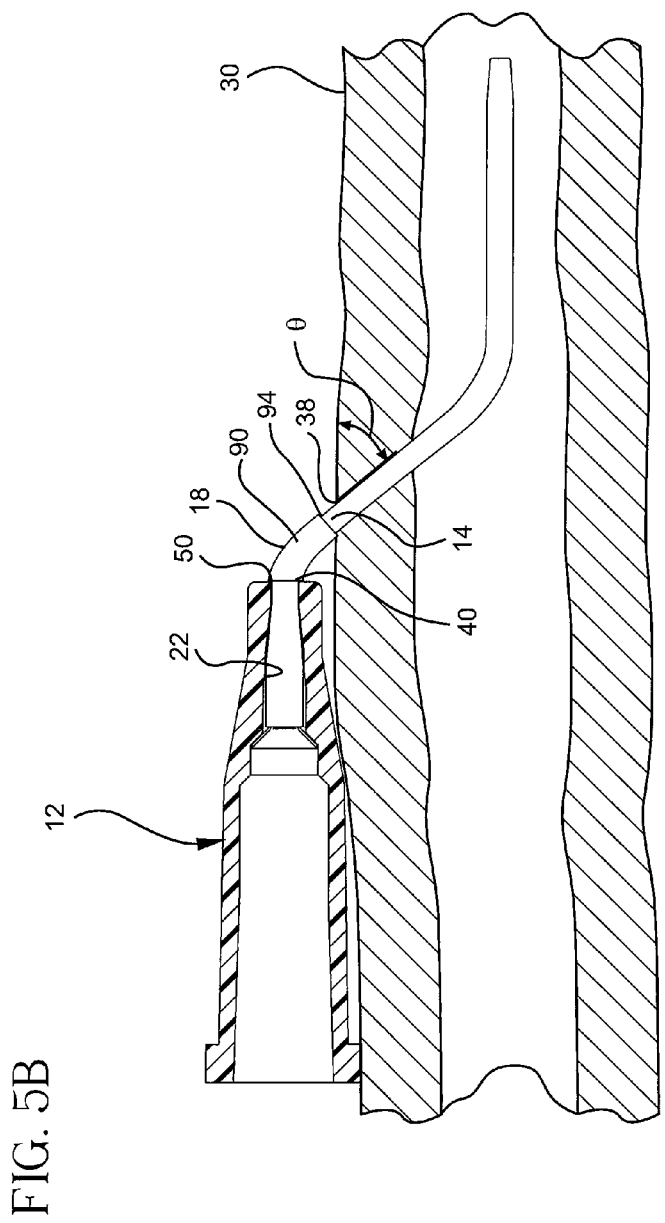
FIG. 5b is a perspective view of a catheter modified to include an external supportive sleeve.

Referring now to FIG. 5b, another embodiment of the catheter 14 is illustrated. In this embodiment, the catheter 14 has been modified to include a semi-flexible sleeve mark 90. The semi-flexible sleeve mark 90 is positioned to indicate a maximum insertion length for the catheter 14. When the catheter 14 is inserted up to the sleeve mark 90, the flexured portion 18 may form a gentle arch thus preventing an occlusion of the catheter 14 at the catheter root 40 due to over-insertion of the catheter 14. In this embodiment, the sleeve mark 90 is an external, physical mark comprising a section of shrink tubing. The sleeve mark 90 is positioned over both the flexured portion 18 and the catheter root 40 of the catheter 14. The sleeve mark 90 is positioned such that the first end 92 of the sleeve mark 90 abuts the catheter adapter tip opening 50. As such, the tolerance between the first end 92 of the sleeve mark 90 and the catheter adapter tip opening 50 is minimal. This sleeve mark 90 further comprises a dual function whereby the sleeve mark 90 indicates a maximum insertion length as well as provides semi-flexible support to the occlusion-prone section of the catheter 14. As such, the sleeve mark 90 aids in the prevention of occlusions.

In one embodiment, the sleeve mark 90 comprises a thin, tubular member of shrink tubing with uniform tube wall thickness. The inner profile of the sleeve mark 90 exactly proximates the outer profile of the catheter 14. The sleeve mark 90 is frictionally attached to the outer surface of the catheter 14 due to the shrunken state of the sleeve mark 90 material. The length of the sleeve mark 90 is chosen to provide an optimal length of uninserted catheter 14 when the catheter 14 is inserted up to the second end 94 of the sleeve mark 90. The sleeve mark 90 further ensures that upon insertion of the catheter 14, the root region 19 of the catheter 14 forms a gentle arch. As such, the gentle arch of the catheter 14 accomplishes an occlusion free transition from the catheter adapter 12 to the insertion site 38.

In another embodiment, the sleeve mark 90 comprises a flexible, yet bulky tubular member of uniform tube wall thickness. In this embodiment, the bulk of the sleeve mark 90 creates a physical barrier. As such the sleeve mark 90 is too bulky to be inserted into the insertion site 38 of the catheter 14. Therefore, the sleeve mark 90 serves as a physical impediment to over-insertion of the catheter 14 thus further preventing an occlusion of the catheter 14 due to over-insertion. Either of the previous embodiments may be modified to include a contrasting color whereby the sleeve mark 90 may serve as a visual indicator to prevent over-insertion of the catheter 14.

In a final embodiment, the sleeve mark 90 comprises a tubular member of shrink tubing with varying tube wall thickness. For example, the first end 92 of the sleeve mark 90 comprises an outer diameter that is greater than the outer diameter of the second end 94 of the sleeve mark 90. As such, the outer surface of the sleeve mark 90 tapers inwardly from the first end 92 to the second end 94. The inner profile of the sleeve mark 90 exactly proximates the outer profile of the catheter 14. As with the other embodiments, the sleeve mark 90 is frictionally attached to the outer surface of the catheter 14 due to the shrunken state of the sleeve mark 90 material.

The tapered feature of the sleeve mark 90 provides varying degrees of flexibility along the length of the sleeve mark 90. As such, an inverse relationship exists between the tube wall thickness and the flexibility of the sleeve mark 90. For example, at any given location along the length of the sleeve mark 90, the greater the thickness of the tube wall, the less flexibility of the sleeve mark 90 at that point. Therefore, the flexibility at the first end 92 of the sleeve mark 90 is less than the flexibility of the second end 94 of sleeve mark 90. The sleeve mark 90 of this embodiment provides less flexibility, and/or more support, to the occlusion-prone catheter root 40 of the catheter 14 and more flexibility and/or less support, to the catheter 14 near the insertion site 38. Finally, this embodiment may also include a sleeve mark 90 of a contrasting color and/or a second end 94 thickness that precludes insertion of the sleeve mark 90 into the insertion site 38. As so configured, the sleeve mark 90 of this embodiment further prevents an occlusion due to over-insertion of the catheter 14.

Figure 5C:
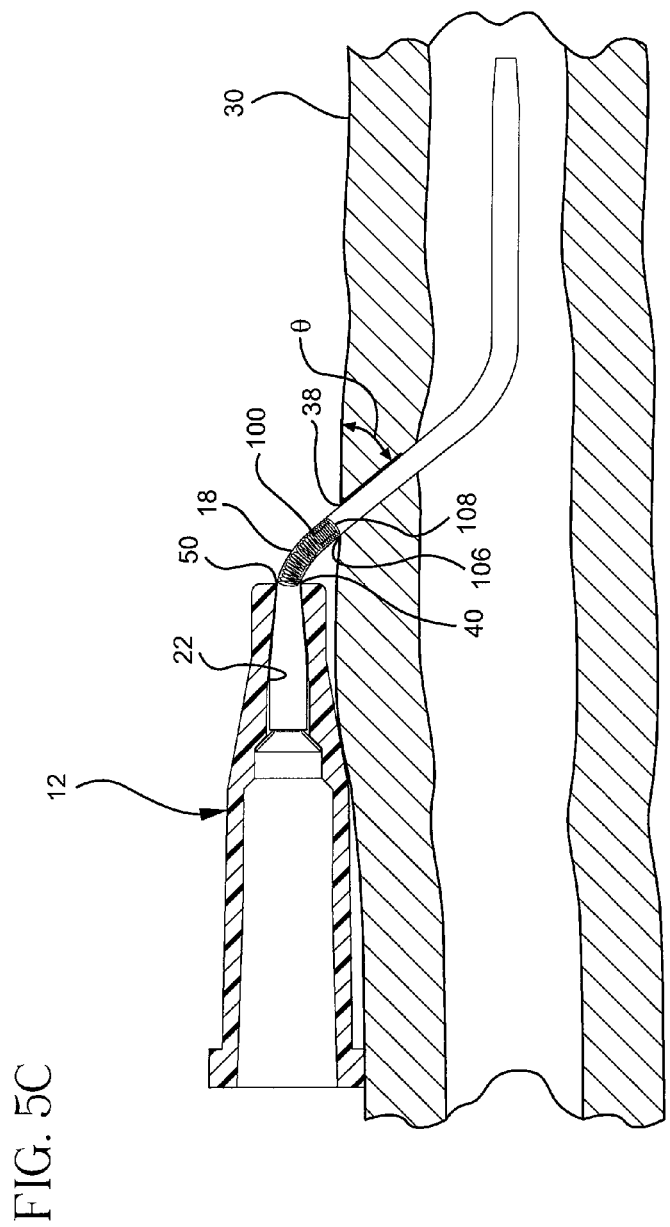
FIG. 5c is a perspective view of a catheter modified to include an internal supportive coil at the catheter's root region.
Figure 5D:
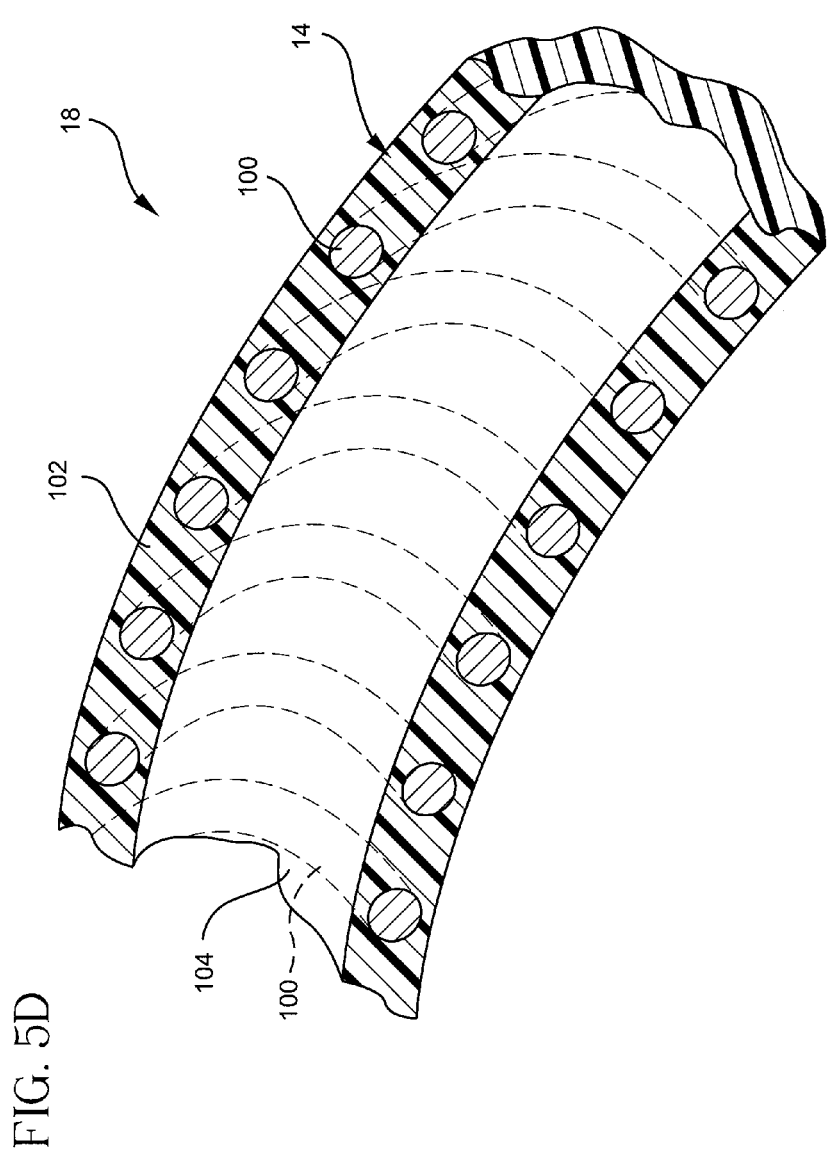
FIG. 5d is a cross-section, detailed view of the internal supportive coil of FIG. 5c.

Referring now to FIGS. 5c and 5d, another embodiment of the catheter 14 is illustrated. In this embodiment, the catheter 14 has been modified to include a supportive spiral 100. The supportive spiral 100 comprises a helical formation of supportive material as formed within the walls 102 of the catheter 14. The supportive material of the spiral 100 may include any rigid, semi-rigid, semi-flexible and/or flexible material that may be incorporated into the walls 102 of the catheter 14 in a helical formation. The supportive spiral 100 is embedded entirely within the walls 102 of the catheter 14. Additionally or alternatively, the supportive spiral 100 may be partially incorporated within the walls 102 of the catheter 14. For either configuration, the supportive spiral 100 is positioned so as to eliminate any interference with the lumen 104 of the catheter 14. The supportive material may also include radiopaque properties such that the portion of the catheter containing the supportive spiral 100 may be radiologically detected.

The coil density of the supportive spiral 100 may vary depending upon the physical properties of the supportive material. Additionally, the coil density may vary based on the desired flexibility of the supportive spiral 100. For example, where a selected supportive material is more flexible, a greater density of coils may be needed in order to achieve the same support of a supportive spiral 100 comprising a more rigid supportive material. Therefore, a more rigid supportive spiral 100 may be achieved by increasing the number of coils per centimeter resulting in a denser coil configuration. Conversely, a more flexible supportive spiral 100 may be achieved by decreasing the number of coils per centimeter resulting in a less dense coil configuration.

The overall number of coils for the supportive spiral 100 may vary depending upon the desired length of the supportive spiral 100. In one embodiment, the length of the supportive spiral 100 is selected such that the supportive spiral 100 extends from the catheter adapter tip 50 to the point of maximum insertion 106. As such, the supportive spiral 100 is of sufficient length to allow the flexured portion 18 to form a gentle arch thereby preventing an occlusion of the catheter 14 at the catheter root 40. In another embodiment, the length of the supportive spiral 100 is selected to extend from the point of maximum insertion 106 to a point internally located within the catheter adapter lumen 22. As such, the supportive spiral 100 comprises a length of the catheter 14 extending into the catheter adapter opening 50. In another embodiment, the terminal end 108 of the supportive spiral 100 is positioned so as to abut the point of maximum insertion 106. As such, the terminal end 108 of the supportive spiral 100 may be used as a visual marker of maximal insertion thereby preventing over-insertion and an occlusion of the catheter 14.

As with the other embodiments of the present invention, the length of uninserted catheter 14, and therefore the point of maximum insertion 106, is selected such that a sufficient length of catheter 14 remains uninserted. This allows the flexured portion 18 of the catheter 14 to gently bend in making the transition from the catheter adapter 12 to the insertion site 38 thereby preventing an occlusion at the catheter root 40.

The present invention may be embodied in other specific forms without departing from its structures, methods, or other essential characteristics as broadly described herein and claimed hereinafter. Additionally, the individual elements of the described embodiments may be interchanged and combined such that any one embodiment may be benefited by the elements of another embodiment. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter apparatus, comprising:
a catheter fixedly attached to a catheter adapter, the catheter adapter having a stepped tip including a top portion and a bottom portion, wherein the top portion of the stepped tip extends outward more than the bottom portion of the stepped tip, and wherein the bottom portion of the stepped tip further comprises a bending surface over which a flexured portion of the catheter is supported to provide an angle of insertion for the catheter without restricting a flow through the catheter.

2. The catheter apparatus of claim 1, wherein the bending surface of the stepped tip is chamfered.

3. The catheter apparatus of claim 1, wherein the bending surface of the stepped tip is rounded.

4. The catheter apparatus of claim 1, wherein the flexured portion of the catheter further comprises an insertion stop mark.

5. The catheter apparatus of claim 4, wherein the insertion stop mark is a contrasting color.

6. The catheter apparatus of claim 4, wherein the insertion stop mark is a section of shrink tubing.

7. The catheter apparatus of claim 4, wherein the insertion stop mark is a spirally wound coil embedded within a wall of the flexured portion of the catheter.

8. The catheter apparatus of claim 4, wherein the insertion stop mark further supports the flexured portion of the catheter in preventing a restriction of the flow through the catheter.

9. The catheter apparatus of claim 1, wherein the top portion of the stepped tip overhangs an insertion site of the catheter.

10. An apparatus for preventing a restricted flow within a catheter, comprising:
a catheter housed within a first end of a catheter adapter, the catheter being fixedly attached to the catheter adapter, the catheter adapter having a stepped tip including a top portion and a bottom portion, the top portion of the stepped tip being extended to overhang an insertion site of a patient; and
a bending surface forming a portion of the first end and supporting a flexured portion of the catheter, the bending surface having an angle within a range of approximately 10° to approximately 60°, wherein the bending surface prevents restriction of a flow through the catheter.

11. The apparatus of claim 10, wherein the flexured portion of the catheter is further supported by an insertion stop mark.

12. The apparatus of claim 11, wherein the insertion stop mark is at least one of an ink printing, a laser printing, an injection molding, a plastic impregnation, a sleeve, a tubular member, and a supportive spiral.

13. The apparatus of claim 10, wherein the angle is approximately 30°.

* * * * *